United States Patent [19]
Gajda

[11] Patent Number: 6,043,402
[45] Date of Patent: *Mar. 28, 2000

[54] METHOD FOR MINIMIZING DIARYLALKANE FORMATION IN ALKYLATION-TRANSALKYLATION PROCESS USING ZEOLITE BETA

[75] Inventor: Gregory J. Gajda, Mount Prospect, Ill.

[73] Assignee: UOP LLC, Des Plaines, Ill.

[*] Notice: This patent is subject to a terminal disclaimer.

[21] Appl. No.: 09/089,563

[22] Filed: Jun. 3, 1998

Related U.S. Application Data

[60] Provisional application No. 60/049,648, Jun. 16, 1997.

[51] Int. Cl.[7] .............................. C07C 5/22; C07C 2/68
[52] U.S. Cl. ............................................ 585/467; 585/475
[58] Field of Search ..................................... 585/467, 475

[56] References Cited

U.S. PATENT DOCUMENTS

| | | | |
|---|---|---|---|
| 2,403,785 | 7/1946 | Britton et al. | 260/671 |
| 2,592,589 | 4/1952 | Nickels | 260/671 |
| 4,008,290 | 2/1977 | Ward | 260/672 T |
| 4,051,191 | 9/1977 | Ward | 260/671 R |
| 4,083,886 | 4/1978 | Michalko | 260/672 T |
| 4,107,224 | 8/1978 | Dwyer | 260/671 R |
| 4,169,111 | 9/1979 | Wight | 585/323 |
| 4,587,370 | 5/1986 | DeGraff | 585/450 |
| 4,695,665 | 9/1987 | DeGraff | 585/450 |
| 4,876,408 | 10/1989 | Ratcliffe et al. | 585/467 |
| 4,891,458 | 1/1990 | Innes et al. | 585/323 |
| 4,922,053 | 5/1990 | Waguespack et al. | 585/449 |
| 5,003,119 | 3/1991 | Sardina et al. | 585/323 |
| 5,030,786 | 7/1991 | Shamshoum et al. | 585/467 |
| 5,177,285 | 1/1993 | Van Opdorp et al. | 585/467 |
| 5,227,558 | 7/1993 | Shamshoum et al. | 585/446 |
| 5,336,821 | 8/1994 | DeGraff et al. | 585/402 |
| 5,522,984 | 6/1996 | Gajda et al. | 208/120 |
| 5,723,710 | 3/1998 | Gajda et al. | 585/467 |
| 5,877,370 | 3/1999 | Gajda | 585/467 |

FOREIGN PATENT DOCUMENTS

| | | |
|---|---|---|
| 0 733 608 A1 | 9/1996 | European Pat. Off. . |
| 0 742 190 A1 | 11/1996 | European Pat. Off. . |
| 19516717 | 11/1996 | Germany . |

OTHER PUBLICATIONS

M.F. Bentham et al. Development and Commercialization of Solid Acid Catalysts DGMK conference on "Catalysis of Solid Acids and Basis" Mar. 14–15, 1996; Berlin, Germany pp. 155–166 (DGMK German Society for Petroleum and Coal Science and Technology) DGMK—Tagungsbericht 9601, ISBN 3–931850–00–5, 1996.

*Primary Examiner*—Walter D. Griffin
*Assistant Examiner*—Thuan D. Dang
*Attorney, Agent, or Firm*—Thomas K. McBride; John G. Tolomei; Michael A. Moore

[57] ABSTRACT

Reduction of the amount of 1,1-diphenylethane formed in the production of ethylbenzene by alkylation of benzene with ethylene and by transalkylation of benzene with polyethylbenzenes can be effected by reacting at a low concentration of ethylene. This invention allows operation at a low molar ratio of phenyl groups per ethyl group and leads to a product containing less than 1.0 wt-% 1,1-diphenylethane relative to ethylbenzene. This invention is applicable to processes for the production of a wide variety of other commercially important alkylated aromatics.

16 Claims, 3 Drawing Sheets

METHOD FOR MINIMIZING DIARYLALKANE FORMATION IN ALKYLATION-TRANSALKYLATION PROCESS USING ZEOLITE BETA

CROSS-REFERENCE TO RELATED APPLICATION

This application claims the benefit of U.S. Provisional Application No. 60/049,648, filed on Jun. 16, 1997.

FIELD OF THE INVENTION

This invention relates to a process for producing monoalkyl aromatic compounds by alkylation and by transalkylation. Specifically, this invention relates to highly-selective alkylation and transalkylation to produce ethylbenzene using zeolite beta.

BACKGROUND OF THE INVENTION

Alkylation of aromatic compounds with a $C_2$ to $C_4$ olefin and transalkylation of polyalkylaromatic compounds are two common reactions for producing monoalkyl aromatic compounds. Examples of these two reactions that are practiced industrially to produce ethylbenzene are the alkylation of benzene with ethylene and the transalkylation of benzene and a diethylbenzene. A simplified summary of the alkylation reaction and its common product and by-products is given below:

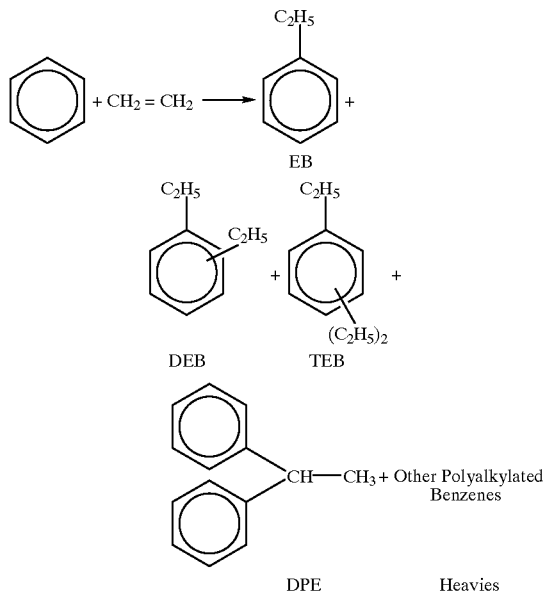

Although the formation of the diethylbenzene and triethylbenzene isomers might, at first glance, be viewed as by-products that represent a reduction in the efficient utilization of ethylene, in fact each can be readily transalkylated by benzene to produce ethylbenzene, as shown below:

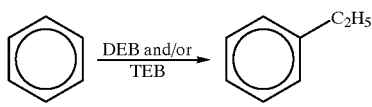

Combining alkylation and transalkylation can thus maximize ethylbenzene production. Such a combination can be carried out in a process having two reaction zones, one for alkylation and the other for transalkylation, or in a process having a single reaction zone in which alkylation and transalkylation both occur. In many cases, a single reaction zone is preferred over two reaction zones because of the savings in capital investment.

One disadvantage of alkylation-transalkylation processes, regardless of whether the alkylation and transalkylation reactions occur in the same or separate reaction zones, is that by-product 1,1-diphenylethane (1,1-DPE) can not be converted to ethylbenzene by alkylation or transalkylation, and thus 1,1-DPE represents a reduction in ethylene utilization efficiency and a loss of ethylene. In fact, the by-production of 1,1-DPE, as well as of the heavier polyethylated benzenes other than diethylbenzene and triethylbenzene which are collectively referred to herein as heavies, represents virtually all of the reduction in the ethylene utilization. The current minimum requirement for combination processes is that 1,1-DPE be not more than 1.0 wt-% relative to ethylbenzene. The formation of 1,1-DPE is assuming added importance and significance in view of the expectation in some areas of near-term minimum standards for the content of 1,1-DPE of not more than 0.5 wt-%.

In reaction zones where alkylation and transalkylation occur, it is known that the formation of 1,1-DPE depends in part on two key operating variables. The first operating variable is the molar ratio of phenyl groups per ethyl group, which is often referred to herein as the phenyl/ethyl ratio. The numerator of this ratio is the number of moles of phenyl groups passing through the reaction zone during a specified period of time. The number of moles of phenyl groups is the sum of all phenyl groups, regardless of the compound in which the phenyl group happens to be. For example, one mole of benzene, one mole of ethylbenzene, and one mole of diethylbenzene each contribute one mole of phenyl group to the sum of phenyl groups. The denominator of this ratio is the number of moles of ethyl groups passing through the reaction zone during the same specified period of time. The number of moles of ethyl groups is the sum of all ethyl and ethenyl groups, regardless of the compound in which the ethyl or ethenyl group happens to be. For example, one mole of ethylene and one mole of ethylbenzene each contribute one mole of ethyl group to the sum of ethyl groups, whereas one mole of diethylbenzene contributes two moles of ethyl groups.

The second operating variable that affects the 1,1-DPE formation is the concentration of ethylene in the alkylation zone. A practical, mathematical approximation is that the concentration of ethylene depends on the molar ratio of phenyl groups per ethyl group according to the formula:

$$[\text{ethylene}] \approx [\text{phenyl/ethyl ratio}]^{-1}.$$

Thus, increasing the phenyl/ethyl ratio decreases the concentration of ethylene.

It is known that a low concentration of ethylene or a high molar ratio of phenyl groups per ethyl group minimizes formation of 1,1-DPE. The amount of 1,1-DPE formed depends on the phenyl/ethyl ratio according to the formula:

$$[1,1\text{-DPE}] \approx [\text{phenyl/ethyl ratio}]^{-2}.$$

Thus, increasing the phenyl/ethyl ratio decreases the amount of 1,1-DPE formed. Although the decrease in 1,1-DPE formation that is conferred by a small increase in phenyl/ethyl ratio may be small, it also is very significant, resulting in a high phenyl/ethyl ratio being the condition of choice for minimizing 1,1-DPE formation. However, a high phenyl/ethyl ratio increases capital and operating costs that are usually associated with the recovery of excess benzene.

These costs give impetus to a search for an ethylbenzene process that minimizes 1,1-DPE formation at a low phenyl/ethyl ratio.

In the prior art, the search for a commercially-viable alkylation process that not only produces a small amount of 1,1-DPE but also operates at a low phenyl/ethyl ratio in the alkylation zone has not been fruitful. All of the prior art processes follow the same, well-known approach of dividing the reaction zone into more and more catalyst beds and injecting smaller and smaller portions of the total ethylene into each bed. Where the allowed concentration of 1,1-DPE is relatively high, this approach undoubtedly confers some benefits. For example, if benzene is alkylated with ethylene in a single-bed alkylation zone that operates at a phenyl/ethyl molar ratio of 5, then the highest concentration of ethylene, which occurs at the point of ethylene injection, is 16.7 mol-%. Downstream of the ethylene injection point, the ethylene concentration decreases to very low concentrations as ethylene is consumed and ethylbenzene is formed, while the phenyl/ethyl ratio remains essentially the same. However, if the single bed is divided into four beds in series and if one-fourth of the required ethylene is injected into each bed, then the phenyl/ethyl ratio is 20 in the first bed, 10 in the second bed, 6.7 in the third bed, and 5 in the fourth bed. Accordingly, the highest concentration of ethylene is 4.8 mol-% in the first bed, 4.5 mol-% in the second bed, 4.3 mol-% in the third bed, and 4.2 mol-% in the fourth bed. Thus, dividing the bed and splitting the ethylene injection increases the phenyl/ethyl ratio and decreases the highest ethylene concentration.

But, in order to operate at the low phenyl/ethyl ratios and to also attain the low concentrations of 1,1-DPE that are expected to become the minimum standard in the near future, this prior art approach is not viable. For example, if benzene is alkylated with ethylene in a four-bed alkylation zone that operates at an overall phenyl/ethyl molar ratio of 2 rather than 5 as in the previous example, then the phenyl/ethyl ratio ranges from 8 in On the first bed to 2 in the fourth bed, and the highest ethylene concentration ranges from 11.1 mol-% in the first bed to 8.3 mol-% in the fourth bed. Compared to the previous example, the ethylene concentration in each bed approximately doubled, which would result in an unacceptable amount of 1,1-DPE formation. In order to reduce the ethylene concentrations to those in the previous example, the number of beds would have to be increased from 4 to 10, simply as a consequence of the fact that the overall phenyl/ethyl ratio had decreased from 5 to 2.

Thus, in response to industry's demands for lower phenyl/ethyl ratios and the market's demand for lower ethylene concentrations, the prior art process inexorably divides the reaction zone into a large number of very small catalyst beds. Because of a variety of technical, economic, and practical considerations, this inefficient solution by the prior art processes is unacceptable in the hydrocarbon processing industry.

SUMMARY OF THE INVENTION

A method has been discovered to significantly reduce the formation of 1,1-DPE in the production of ethylbenzene by alkylation and transalkylation using zeolite beta at a low molar ratio of phenyl groups per ethyl group (phenyl/ethyl ratio). This invention can use one or more components or portions of the reaction zone effluent stream that are capable of transalkylating with benzene to produce ethylbenzene to dilute the ethylene concentration in the reaction zone and consequently to decrease the 1,1-DPE formation. This result using zeolite beta was surprising and was not predictable from the prior art, which teaches that 1,1-DPE formation can be reduced only by increasing the phenyl/ethyl ratio or by increasing the number of catalyst beds. Moreover, prior art processes using Y zeolite produce more 1,1-DPE and deactivate more rapidly as a result of using the same polyalkyl aromatic components and streams that confer benefits on this invention which uses zeolite beta. A process of alkylating benzene with ethylene and transalkylating benzenes with polyethylbenzenes at a low ethylene concentration shows a significant selectivity advantage over one operating at a high ethylene concentration. By using this invention, ethylbenzene processes can now minimize 1,1-DPE formation even when operating at low molar ratios of phenyl groups per ethyl group. With the problem of 1,1-DPE formation now solved by this invention, ethylbenzene processes can now operate more profitably at a low molar ratio of phenyl groups per ethyl group.

The working hypothesis for the underlying chemistry responsible for the observed results is that in the alkylation of an aromatic by an olefin, when the concentration of an olefin decreases, there is a selective decrease in the reaction between the olefin and the alkyl aromatic. The products of this reaction are an alkenyl aromatic and a paraffin that correspond to the olefin. The alkenyl aromatic can in turn serve as an active alkylating agent and react with the aromatic to form by-product diarylalkane. The outcome of the foregoing hypothesis and its logical consequence is that one can expect a decrease in the olefin concentration to confer benefits generally upon the alkylation of aromatics with olefins. Applying this hypothesis to the alkylation of benzene with ethylene, the apparently anomalous formation of 1,1-DPE probably results from the following reaction:

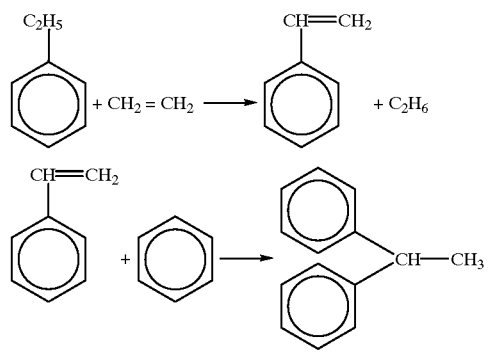

Where a catalyst is used, it is believed that the ethylbenzene and the styrene are chemisorbed on the catalyst, and that hydrogen transfer occurs from the ethylbenzene to ethylene. In any event, a decrease in the concentration of ethylene affords a decrease in the formation of styrene and in turn that of 1,1 -DPE.

This invention minimizes 1,1-DPE formation by using a polyethylbenzene in the combined feed to the reaction zone to transalkylate with benzene and to prevent the ethylene concentration from ever attaining the high ethylene concentrations that are present in prior art processes. It is generally known that in prior art processes the concentration of ethylene in the reaction zone decreases from a relatively high concentration at the inlet point where ethylene is introduced to a relatively low concentration at the outlet where nearly all of the ethylene has been consumed. So, even in the prior art processes, low concentrations of ethylene can occur, especially near the outlet of the reaction zone. However, it has been discovered that even the localized high ethylene concentrations that occur in prior art processes at the point of ethylene injection produce unacceptably high concentrations of 1,1-DPE. Thus, it is now recognized that a polyalkyl aromatic can preclude localized high ethylene concentrations and minimize 1,1-DPE formation. Moreover, it has been recognized that some polyalkyl aromatics are preferred over other polyalkyl aromatics and that selective choice of this polyalkyl aromatic can decease not only the molar ratio of phenyl groups per ethyl group but also the formation of other undesirable by-products besides 1,1-DPE.

This working hypothesis explains the formation of other diarylalkanes that correspond to other olefins alkylating other aromatics. For example, in the alkylation of benzene with propylene to produce cumene, the corresponding diarylalkane would probably be 2,2-diphenylpropane (2,2-DPP). Although formation of 1,1-diphenylpropane (1,1-DPP) is also possible, 2,2-DPP formation is believed to be more probable because of isomerization of the propyl group.

It is a broad object of this invention to improve the selectivity of and to decrease the costs of processes for the alkylation of aromatics with olefins and the transalkylation of aromatics with polyalkyl aromatics. It is a specific object of this invention to minimize the formation of 1,1-diphenylethane (1,1-DPE) in alkylation-transalkylation processes that produce ethylbenzene. It is another specific object of this invention to decrease costs associated with operating alkylation-transalkylation processes by decreasing the molar ratio of phenyl groups per alkyl group at alkylation-transalkylation conditions.

In a broad embodiment, this invention is a process for producing an monoalkyl aromatic. An aromatic, an olefin, and a polyalkyl aromatic comprising at least one phenyl group and at least two alkyl groups corresponding to the olefin are passed to a reaction zone. In the reaction zone, the aromatic is alkylated with the olefin and the aromatic is transalkylated with the polyalkyl aromatic in the presence of zeolite beta to form a monoalkyl aromatic. The reaction conditions include a molar ratio of phenyl groups per alkyl group of from about 0.75:1 to about 25:1 and a concentration of the olefin of less than $$\frac{MW_O}{6.17 \times MW_A + MW_O}, wt-\%$$

wherein $MW_O$ is the molecular weight of the olefin and $MW_A$ is the molecular weight of the aromatic. These reaction conditions inhibit the formation of diarylalkane corresponding to the olefin. A product comprising the monoalkyl aromatic is withdrawn from the reaction zone.

In a more specific embodiment, this invention is a process for producing ethylbenzene. Benzene, ethylene, and a polyalkyl aromatic comprising at least one phenyl group and at least two ethyl groups are passed to a reaction zone. Benzene is alkylated with ethylene and benzene is transalkylated with the polyalkyl aromatic in the reaction zone in the presence of zeolite beta to form ethylbenzene. The reaction conditions include a molar ratio of phenyl groups per ethyl group of from about 1:1 to about 6:1 and a concentration of ethylene of less than 5.5 wt-%. A product comprising ethylbenzene and the polyalkyl aromatic is withdrawn from the reaction zone. The product contains less than 1.0 wt-% 1,1-diphenylethane relative to ethylbenzene. The polyalkyl aromatic is separated from the product and is recycled to the reaction zone.

In another more specific embodiment, this invention is a process for the production of ethylbenzene. Ethylene, an input stream comprising benzene, and a recycle stream combine to form a combined stream. The combined stream passes to a reaction zone containing a catalyst comprising zeolite beta and that operates at reaction conditions sufficient to alkylate benzene with ethylene and to transalkylate benzene with diethylbenzene. The reaction conditions include a molar ratio of phenyl groups per ethyl group of from about 1:1 to about 6:1 and a concentration of ethylene of less than 5.5 wt-%. An effluent stream comprising benzene, ethylbenzene, diethylbenzene, and a heavy polyalkylaromatic is recovered from the reaction zone. The effluent stream contains less than 1.0 wt-% 1,1-diphenylethane relative to ethylbenzene. At least a portion of the effluent stream passes to a separation zone where the effluent stream is separated. Three streams are withdrawn from the separation zone: a low-boiling fraction comprising benzene, a product stream comprising ethylbenzene, and a high-boiling fraction comprising diethylbenzene and the heavy polyalkylaromatic. The product stream is recovered from the process. A portion of the input stream is provided from at least a portion of the low-boiling fraction. The recycle stream is formed from a portion of the effluent stream or at least a portion of the high-boiling fraction.

INFORMATION DISCLOSURE

Prior art alkylation processes are well described in the literature.

U.S. Pat. No. 4,051,191 describes catalysts, reaction conditions, and a separation method for the recovery of cumene that uses a rectification zone and a two-column fractionation train.

U.S. Pat. Nos. 4,695,665 and 4,587,370 are particularly directed to the separation of products and the recovery of recycle streams from processes for the alkylation of aromatic hydrocarbons, and U.S. Pat. No. 4,695,665 discloses the use of a flash drum in combination with an effluent rectifier to recover unreacted feed components.

U.S. Pat. No. 4,876,408 discloses an alkylation process that uses zeolite beta having carbon deposits thereon to suppress alkylation activity and increase selectivity to monoalkylate.

U.S. Pat. No. 4,891,458 describes the use of beta zeolite for the alkylation of aromatic hydrocarbons with alkenes to produce alkyl aromatics. U.S. Pat. No. 4,891,458 is also discloses that transalkylation can occur in an alkylation reactor, and that additional monoalkyl aromatic hydrocarbons can be produced in an alkylation reactor by recycling polyalkyl aromatic hydrocarbons to the alkylation reactor to undergo transalkylation.

U.S. Pat. No. 4,922,053 describes a process for alkylating benzene with ethylene in a multibed reactor wherein polyethylbenzenes are recycled to the first alkylation bed and also to one or more of the other alkylation beds in order to increase ethylbenzene yield.

U.S. Pat. No. 5,030,786 discloses an alkylation process wherein the feed stream is dehydrated to enhance the performance of beta or Y zeolites in the alkylation process.

U.S. Pat. No. 5,227,558 discloses an alkylation process for the production of ethylbenzene that uses a steam modified zeolite beta catalyst.

U.S. Pat. No. 5,336,821 describes the use of beta zeolite for the alkylation of aromatic hydrocarbons in a process that is improved by an indirect heat exchanger to recover the heat of reaction. In one embodiment, the alkylation reactor effluent passes through the heat exchanger and is recycled to the alkylation reactor.

Prior art transalkylation processes are well described in the literature. U.S. Pat. No. 4,083,886 describes a process for the transalkylation of the alkyl aromatic hydrocarbons that uses a zeolitic catalyst. U.S. Pat. No. 4,891,458 describes the use of beta zeolite for the transalkylation of aromatic hydrocarbons with polyalkyl aromatic hydrocarbons. European Patent Application EP 0 733 608 A1 discloses the use of an alumina silicate catalyst having an average crystal size of less than about 0.5 microns for the transalkylation of polyalkyl benzenes with benzene in a reaction zone with an alkylating agent such as ethylene.

Combination processes that produce alkyl aromatic products by using an alkylation reaction zone and a transalkylation reaction zone are also well known.

U.S. Pat. No. 4,008,290 describes a combination process in which the alkylation effluent and the transalkylation effluent are passed to a common separation zone, which separates the two effluents into product, by-product, and recycle streams including a recycle benzene stream. A portion of the alkylation effluent is recycled to the alkylation reaction zone in order to decrease the portion of the recycle benzene stream that is recycled to the alkylation reaction zone. The teachings of U.S. Pat. No. 4,008,290 are incorporated herein by reference.

U.S. Pat. No. 5,003,119 describes a combination process for producing monoalkyl aromatics in which the alkylation effluent passes to the transalkylation reaction zone, and the transalkylation effluent passes to a separation zone. U.S. Pat. No. 5,003,119 also describes passing dialkyl aromatics to the alkylation reaction zone. In addition, U.S. Pat. No. 5,003,119 teaches that diphenylalkanes are alkylation by-products and that a zeolitic catalyst can be used to convert diphenylalkanes into lighter aromatics.

U.S. Pat. No. 5,177,285 discloses an alkylation process that is improved by maintaining the feed to the alkylation zone in a relatively wet condition and the feed to the transalkylation zone in a relatively dry condition. The process operates with a relatively pure ethylene feed as an alkylating agent with a large excess of benzene.

German Patent Application DE 19,516,717 discloses the preparation of 1,1 diphenylethanes by the addition reaction of benzene with styrene in the presence of beta zeolite.

A paper entitled "Development and Commercialization of Solid Acid Catalysts," by M. F. Bentham et al., was presented at the DGMK meeting on "Catalysis of Solid Acids and Bases" on Mar. 14–15, 1996, in Berlin, Germany, and describes the formation of diphenylethane in ethylbenzene processes by the reaction of benzene and ethylene to form styrene and ethane and by the reaction of benzene and styrene to form diphenylethane.

DETAILED DESCRIPTION OF THE INVENTION

Figure 1:
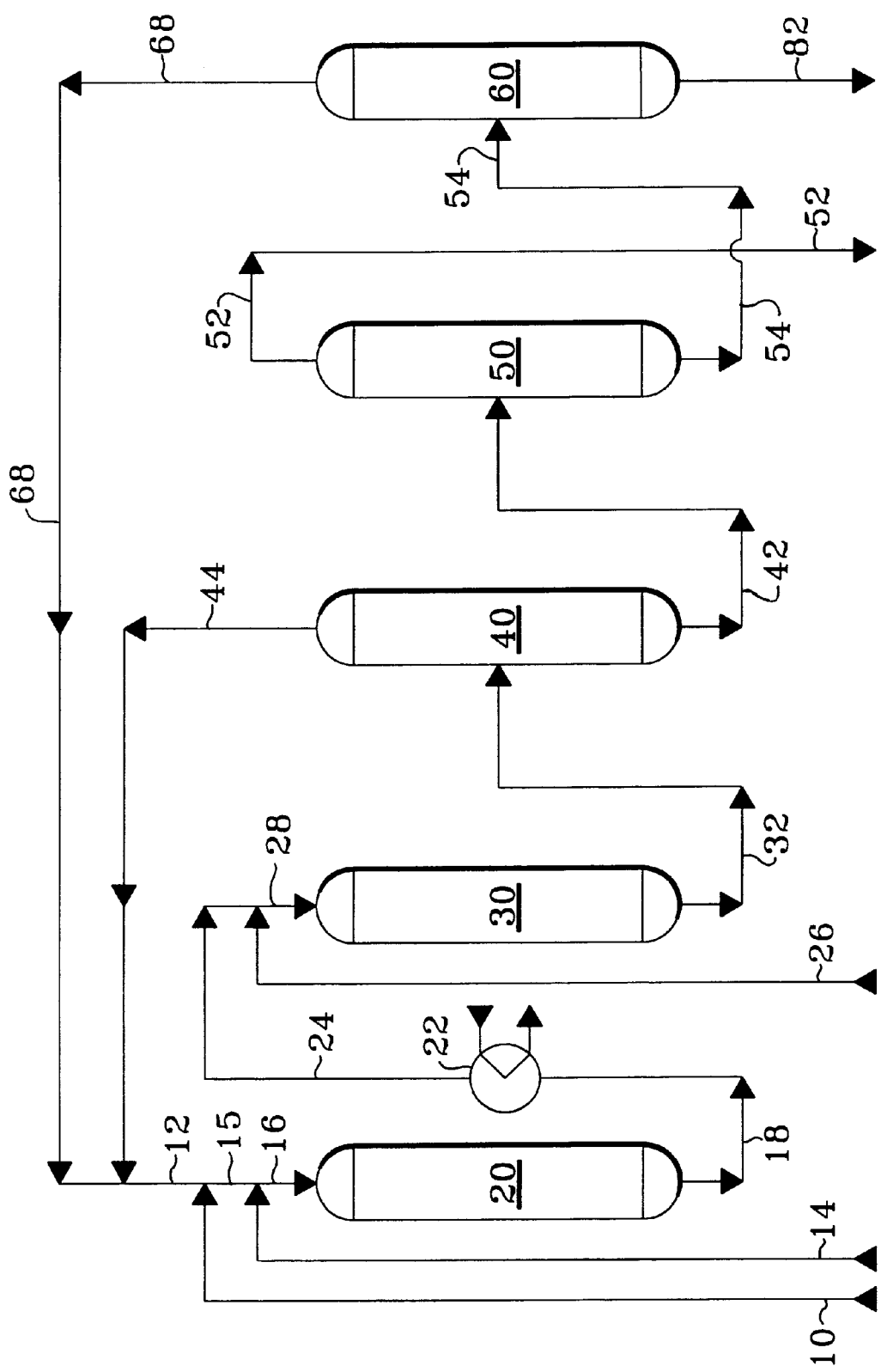
FIG. 1 is a schematic illustration of a preferred embodiment of this invention.

As discussed previously, this invention can be expected to be applicable generally to the alkylation of an alkylation substrate with an alkylation agent in the presence of a transalkylation agent. This invention is more specifically applicable to the production of an alkylaromatic by alkylation of an aromatic with an olefin and by transalkylation of an aromatic with a polyalkylaromatic. Although benzene is the principal aromatic of interest, aromatics such as alkyl-substituted benzenes, condensed ring systems generally, and alkylated derivatives thereof may be used. Examples of such aromatics are toluene, ethylbenzene, propylbenzene, and so forth; xylene, mesitylene, methylethylbenzene, and so on; naphthalene, anthracene, phenanthrene, methylnaphthalene, dimethyinaphthalene, and tetralin. More than one aromatic can be used.

Olefins containing from 2 to 6 carbon atoms are the principal alkylating agents contemplated for this invention. Examples of such olefins include ethylene, propylene, butene-1, cis-butene-2, trans-butene-2, and iso-butene. However, olefins having from 2 to 20 carbon atoms may be used effectively in this invention. More than one olefin may be used.

The most widely practiced hydrocarbon conversion process to which the present invention is applicable is the catalytic alkylation of benzene with ethylene to produce ethylbenzene. Therefore, the discussion herein of the present invention will be in reference to its application to a catalytic ethylbenzene reaction system. It is not intended that this discussion limit the scope of the present invention as set forth in the claims.

In theory, the transalkylation agent may be any compound that is capable of transalkylating with the alkylation substrate (e.g., benzene), mixing with the alkylating agent (e.g., ethylene), and decreasing the concentration of the alkylating agent at and downstream of the alkylation agent injection point. In practice, however, the transalkylation agent should have a number of possible characteristics that are consistent with the process objective of producing high yields of high-purity product ethylbenzene. First, the transalkylation agent should increase ethylbenzene yield by transalkylation, in addition to increasing ethylbenzene yield by minimizing 1,1-DPE formation. Accordingly, a polyethylbenzene, such as diethylbenzene, triethylbenzene, and so forth up to even hexaethylbenzene, is preferred because each can transalkylate to ethylbenzene, regardless of whether each is alkylated by ethylene. Because of the possibility of alkylation of the polyethylbenzene by ethylene, however, the lighter polyethylbenzenes are more preferred over the heavier polyethylbenzenes, with diethylbenzene being most preferred.

A second characteristic of the transalkylation agent is that the transalkylation agent should decrease the molar ratio of phenyl groups per ethyl groups in the reaction zone. This is usually not a limiting characteristic, however, because if the transalkylation agent has at least one phenyl group and one ethyl group, then the transalkylation agent will decrease the phenyl/ethyl ratio if the ratio is greater than 1. Transalkylation agents with two or more ethyl groups per phenyl will decrease the phenyl/ethyl ratio if the ratio is greater than 0.5, and so on for transalkylation agents with more ethyl groups per phenyl group. Third, the transalkylation agent should not adversely affect ethylbenzene yield. For example, toluene and cumene are not preferred, because ethylene can alkylate toluene or cumene and produce by-products that cannot be converted readily to ethylbenzene by alkylation or transalkylation. Ethylbenzene is also not preferred, because ethylbenzene can shift the equilibrium of the reactions away from the formation of ethylbenzene and because ethylbenzene can react with ethylene to produce styrene and ultimately 1,1-DPE. Fourth, the transalkylation agent should not adversely affect ethylbenzene purity. For example, xylenes are not preferred because they are relatively difficult to separate from ethylbenzene by distillation. Another reason that xylenes are not preferred is that they can adversely affect ethylbenzene yield by alkylating with ethylene.

In general, the transalkylation agent is preferably a compound that corresponds to the alkylation substrate alkylated with at least one more alkyl group corresponding to the alkylation agent than the number of alkyl groups on the desired product of alkylating the alkylation substrate with the alkylating agent. In the general case, the transalkylation agent is different from the desired product of alkylating the alkylation substrate with the alkylation agent. Where the aromatic is benzene and the olefin is ethylene, the transalkylation agent can generally be a polyalkylbenzene having two or more ethyl groups. Suitable transalkylation agents include di-, tri-, and tetra-ethyl aromatic hydrocarbons such as diethylbenzene, triethylbenzene, diethylmethylbenzene, diethylpropylbenzene, etc. Diethylbenzenes, especially ortho-, meta-, and para-diethylbenzenes, are especially preferred transalkylation agents.

The alkylation and transalkylation reactions take place at a molar ratio of phenyl groups per alkyl group of from 25:1 to about 1:1. The molar ratio may be less than 1:1, and it is believed that the molar ratio may be 0.75:1 or lower. In this invention, successful operation at low molar ratio of phenyl groups per ethyl group, e.g., below 6:1, is achieved by introducing the polyalkyl aromatic to the reaction zone so that the concentration of ethylene remains less than 5.5 wt-%. By contrast, in prior art processes for the alkylation of benzene with ethylene, if the molar ratio of phenyl groups per ethyl group is 6.17, then ethylene constitutes 5.5 wt-% of the total weight of hydrocarbons, namely benzene and ethylene, that is passed to the alkylation reaction zone. In the general case for alkylating agents other than ethylene and alkylation substrates other than benzene, successful operation in accord with this invention at a low molar ratio of phenyl groups per alkyl group is achieved by introducing the polyalkyl aromatic to the reaction zone so that the concentration in weight percent of olefin remains less than that computed by the following formula:

$$\frac{MW_{AA}}{6.17 \times MW_{AS} + MW_{AA}}, \text{wt} - \%,$$

where $MW_{AA}$ is the molecular weight of the alkylation agent (e.g., olefin) and $MW_{AS}$ is the molecular weight of the alkylation substrate (e.g., benzene).

In general, for a given molar ratio of alkylation substrate per alkylation agent, the greater the molar ratio of phenyl groups to alkyl groups in the feed stream, the less is the rise in temperature in the reaction zone that occurs as a result of the alkylation reactions. The alkylation reactions have a heat of reaction of 100–150 BTU/lb-mole and are considered to be moderately exothermic. Although the reactor may have indirect heat exchange means to remove the heat as it is produced, the reactor is preferably adiabatic, and so the outlet temperature of the effluent stream is higher than the inlet temperature of the reactants. An increase in the molar ratio of phenyl groups to alkyl groups in the feed stream increases the quantity of phenyl groups available to act as a heat sink in the reaction zone and thus decreases the temperature rise in the reaction zone. Thus, in practicing this invention, the inlet temperature in the reaction zone is generally from 392 to 500° F. (200 to 260° C.), and preferably from 446 to 482° F. (230 to 250° C.). Although the temperature rise that occurs in the reaction zone could be from 18 to 342° F. (10 to 190° C.) depending on the total mass flows in the reactor, the temperature rise is generally from 9 to 90° F. (5 to 50° C.), and preferably from 9 to 36° F. (5 to 20° C.). In general, reaction temperature is generally from 212° F. (100° C.) to the critical temperature of the alkylation substrate, which may be 887° F. (475° C.) or even higher.

As described previously, the temperature rise in the reaction zone may be controlled by adjusting the molar ratio of phenyl groups to ethyl groups in the feed stream. Minimizing the temperature rise helps prevent high reactor outlet temperatures, which cause undesirable side reactions such as cracking of hydrocarbons to occur. High reaction temperatures can also cause vaporization of benzene and ethylbenzene in the reaction zone. In one embodiment of this invention, the temperature rise in the reaction zone can be controlled by withdrawing an effluent stream from the reaction zone, cooling a portion of the effluent stream, and recycling the cooled portion of the effluent stream to the reaction zone. Although recycling reactor effluent to the reaction zone in this manner may be disadvantageous for some reaction zones, it is not disadvantageous for this invention because recycling reactor effluent to the reaction zone does not significantly alter the product distribution when the catalyst is zeolite beta. A significant alteration in the product distribution is a change in the concentration of any of the products in the reactor effluent stream of more than 0.5 wt-%. A significant alteration in the product distribution does not occur because at the reaction conditions zeolite beta is such an active promoter of the alkylation reaction between benzene and ethylene and of the transalkylation reaction between benzene and diethylbenzene that the extent of reaction proceeds at least 80% and generally more than 90% of the way to equilibrium. Thus, recycling reactor effluent to the reaction zone does not interfere in a significant way with the extent of the alkylation or transalkylation reactions, and recycling reactor effluent may be employed for the purpose of controlling reaction zone temperatures.

Alkylation and transalkylation are preferably performed in the liquid phase. Consequently, reaction pressure needs to be sufficiently high to ensure at least a partial liquid phase. Where ethylene is the olefin, the pressure range for the reactions is usually from about 200 to about 1000 psi(g) (1379 to 6985 kPa(g)), more commonly from about 300 to about 600 psi(g) (2069 to 4137 kPa(g)), and even more commonly from about 450 to about 600 psi(g) (3103 to 4137 kPa(g)). Preferably, the reaction conditions are sufficient to maintain benzene in a liquid phase and are supercritical conditions for ethylene. Pressure is not a critical variable in the success of this invention, however, and the only criterion is that the pressure be sufficiently great to ensure at least partial liquid phase. For olefins other than ethylene, this invention may be practiced generally at a pressure of from 50 to 1000 psi(g) (345 to 6985 kPa(g)).

The weight hourly space velocity of ethylene may range from 0.01 to 2.0 hr$^{-1}$. The weight hourly space velocity of aromatics, including benzene and a polyalkylaromatic having at least two $C_2$+groups, is generally from 0.3 to 480 hr$^{-1}$. In a preferred embodiment, in which the polyalkyl aromatic is a diethylbenzene or a triethylbenzene, the molar ratio of benzene per ethylene is from 2:1 to 6:1, the weight hourly space velocity of ethylene is from 0.1 to 1.0 hr$^{-1}$, and the weight hourly space velocity of aromatics, including benzene and the polyethylbenzenes is from 0.5 to 19 hr$^{-1}$.

The principal reactions that occur in the reaction zone are the alkylation of the benzene by ethylene and the transalkylation of benzene with a polyethylbenzene to produce ethylbenzene. In addition, other reactions can occur in the reaction zone. For example, the polyethylbenzene can be alkylated with ethylene. Although the extent to which these other reactions form by-products is diminished by the practice of this invention, the reactor effluent stream nevertheless usually contains the by-products of these other reactions. Accordingly, a portion of the reactor effluent stream can be used without any downstream separation as a stream for supplying polyethylbenzene to the alkylation reaction zone. Alternatively, the reactor effluent stream can be passed to a separation zone from which can be recovered a fraction containing one or more components that are suitable polyethylbenzenes, and this fraction can in turn be passed to the reaction zone. In view of the previous discussion that identified certain compounds as preferred polyethylbenzenes, it follows that in a commercial ethylbenzene process certain process streams are preferred for supplying the polyethylbenzene to the reaction zone. Hereinafter-described FIGS. 1, 2, and 3 identify these preferred process streams.

The reactor effluent stream contains ethylbenzene and may also contain unreacted polyethylbenzene or a by-product of an alkylation side reaction involving the polyethylbenzene or a by-product of a transalkylation side reaction involving the polyethylbenzene. The reactor effluent stream may also contain unreacted benzene as well as a by-product of an alkylation side reaction involving benzene or a by-product of a transalkylation side reaction involving benzene. In addition, the reactor effluent stream may contain unreacted ethylene, but the concentration of unreacted ethylene is likely to be insignificant because benzene is usually present at least in a stoichiometric proportion. Although it is not common for the feed stream to contain $C_1$ to $C_3$ paraffins in addition to ethylene, if ethane is present in the feed stream then the reactor effluent stream may also contain unreacted ethane.

The reactor effluent stream passes to a separation zone, which generally comprises a benzene fractionation column in order to recycle unreacted benzene to the alkylation zone, and an ethylbenzene fractionation column in order to recover ethylbenzene as product from the heavier polyalkylbenzenes. A polyalkylbenzene fractionation column may also be used in order to separate diethylbenzenes and triethylbenzenes from the other heavier polyalkylbenzenes, particularly where the polyalkylbenzene that is present in the feed stream is a diethylbenzene or a triethylbenzene. The separation zone generally does not comprise a deethanizer unless the concentrations of unreacted ethylene, ethane, or light $C_3$– paraffins in the reactor effluent are high enough to justify their being separated from the reactor effluent stream.

The catalyst for the present invention may be any alkylation catalyst that is not deactivated rapidly as a consequence of recycling the polyalkyl aromatic to the alkylation reactor. Recycling of the polyalkyl aromatic can accelerate deactivation of the catalyst in two ways: first, the polyalkyl aromatic is itself a heavy alkylated aromatic compound that deactivates the catalyst; or second, the polyalkyl aromatic is recycled in a stream that contains other compounds that are heavy alkylated aromatic compounds and that deactivate the catalyst. The catalyst for the present invention may be one of a class of aluminosilicate molecular sieves known as zeolites. The zeolitic molecular sieves suitable for use in the present invention are crystalline aluminosilicates which in the calcined form may be represented by the general formula:

$$Me_{2/n} O: Al_2O_3: xSiO_2:yH_2O$$

where Me is a cation, n is the valence of the cation, x has a value of from about 5 to 100, and y has a value of from about 2 to 10. Detailed descriptions of zeolites may be found in D. W. Breck, Zeolite Molecular Sieves, John Wiley and Sons, New York 1974, and in other standard references. Suitable zeolites are zeolite beta as disclosed in U.S. Pat. Nos. 4,891,458 and 5,081,323, the teachings of which are incorporated herein by reference, and a steamed and ammonium exchanged zeolite beta as disclosed in U.S. Pat. No. 5,522,984, the teachings of which are incorporated herein by reference. It is believed that mordenite and zeolite omega can also be suitable catalysts for this invention.

A preferred zeolite for use in this invention is a surface-modified zeolite beta which results from acid washing of a templated native zeolite beta. That is, the formation of the surface-modified zeolite beta starts with a templated beta where the template is, for example, a tetraalkylammonium salt, such as tetraethylammonium salt. It is critical to acid wash a templated zeolite beta in order to protect the internal sites of the zeolite and to prevent dealumination. The templated zeolite beta is treated with a strong acid at a pH between about 0 up to about 2, although a pH under 1 is preferred. Acids which may be used include nitric acid, sulfuric acid, phosphoric acid, and so forth. For example, a weak, 0.01 molar nitric acid may be used in conjunction with ammonium nitrate to perform the acid wash, although substantially higher concentrations, up to about 20 weight percent nitric acid, are preferred. Nitric acid is a preferred acid since it is a non-complexing acid and therefore does not encourage dealumination. Treatment of the templated zeolite beta with strong acid may be effected over the temperature range between about 20° C. up to about 125° C. It is important that acid washing be done under conditions not so severe as to effect dealumination.

The time over which acid washing is conducted in preparing the preferred zeolite is quite temperature dependent. It is critical in the formation of the surface-modified zeolite beta that there be no significant bulk dealumination of the zeolite. Thus, as a general statement it can be said that acid washing should be done for a time insufficient to effect dealumination. For example, using 0.01 molar nitric acid and circa 40% ammonium nitrate at 70° C., contact times of 2–3 hours are found adequate to modify the environment of surface aluminum without causing significant bulk dealumination. Using circa 15% nitric acid with ammonium nitrate to treat a circa 25 weight percent slurry at 85° C., a 90-minute treatment is effective. The dependent variables in acid washing include acid concentration, slurry concentration, time and temperature, and suitable conditions at which surface-modified zeolite beta can be prepared without significant bulk dealumination are readily determined by the skilled artisan.

Next the template is removed by calcination at temperatures in the range of 550–700° C. Calcination conditions are well known in the art and need not be elaborated upon here. It also needs to be mentioned that powdered zeolite itself is not usually used as the alkylation catalyst. Therefore, in the more usual case after the templated zeolite beta is acid washed it is mixed with a conventional binder, extruded, and the extrudate is ultimately calcined. But the critical portion of the preparation of the preferred zeolite is the acid wash of the templated beta according to the foregoing description. Acid washing a calcined (i.e., non-templated) zeolite beta does not afford the surface-modified material of the preferred zeolite.

It has been found that after treatment as described above the surface aluminum atoms are chemically modified. It has been hypothesized that the modification is in the form of replacement of strong acid sites at the catalyst surface by weaker acid sites. What has been definitely observed is that the surface aluminums of the preferred modified zeolite beta have 2p binding energies as measured by x-ray photoelectron spectroscopy of at least 74.8 electron volts.

Figure 2:
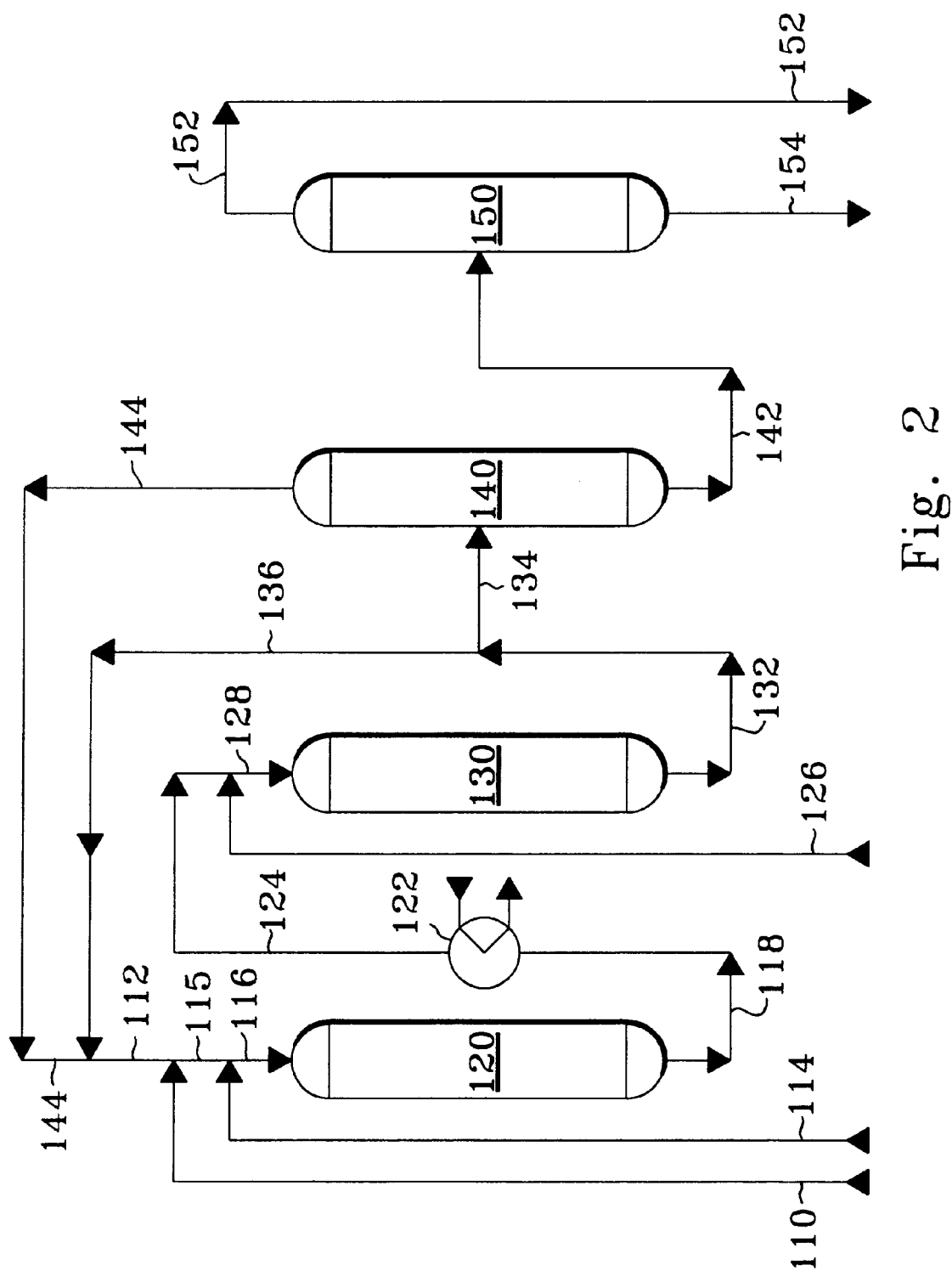
FIGS. 2 and 3 are schematic illustrations of other embodiments of this invention.
Figure 3:
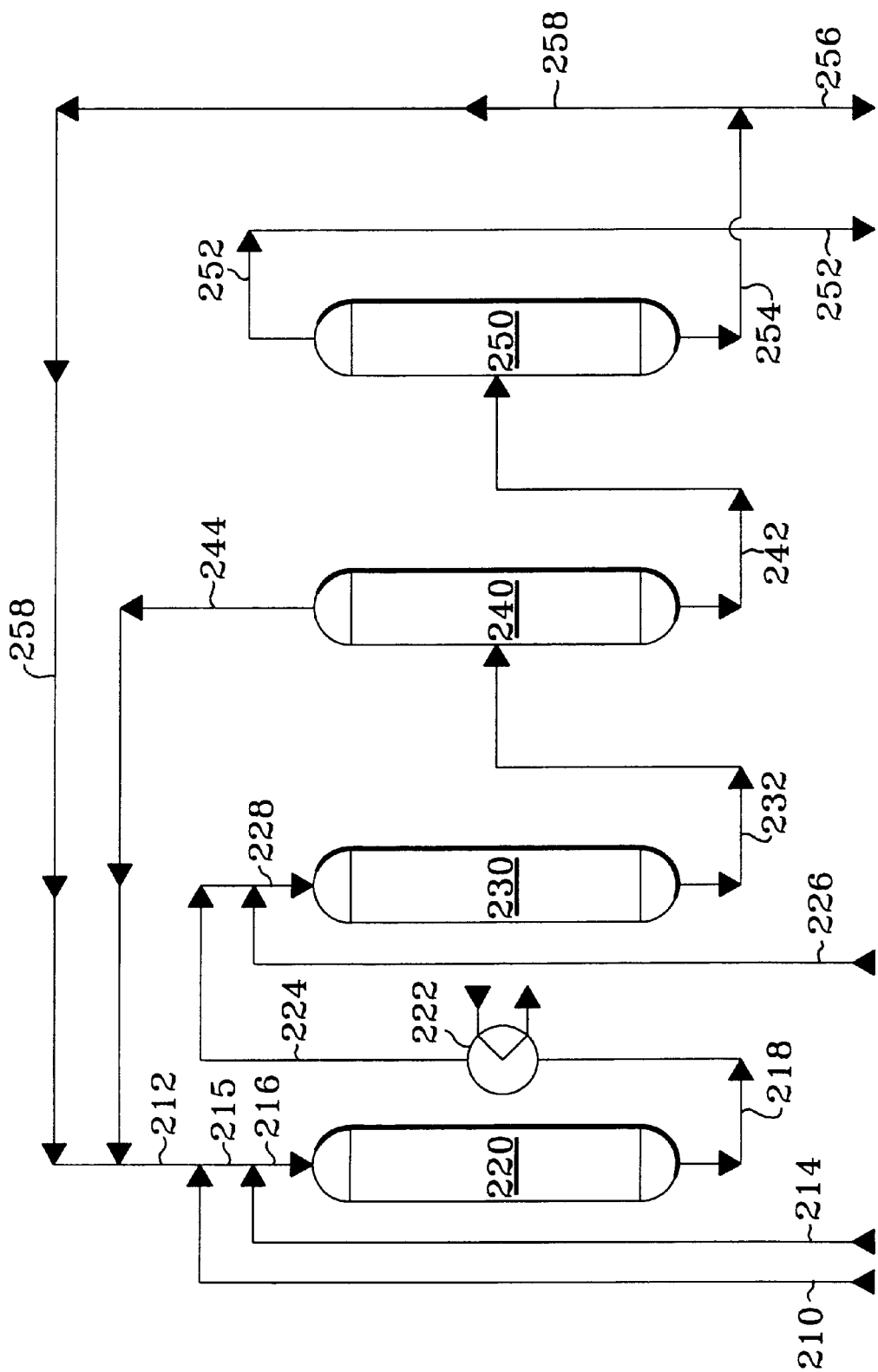

FIGS. 1, 2, and 3 illustrate three embodiments of the invention. For clarity and simplicity, some items associated with the operation of the process have not been shown. These items include flow and pressure control valves, pumps, heat exchangers, temperature and pressure monitoring systems, reactor and fractionator internals, etc., which may be of customary design. Such representation of these embodiments is not intended to limit the scope of the present invention as set forth in the claims.

Referring now to FIG. 1, FIG. 1 illustrates a preferred embodiment of this invention in which a polyethylbenzene column overhead stream is recycled to the alkylation-transalkylation reactor. The overhead stream of the polyethylbenzene column typically contains only diethylbenzenes and triethylbenzenes. One advantage of this embodiment is that the overhead stream of the polyethylbenzene column contains a relatively low concentration of ethylbenzene, which is not a polyethylbenzene and cannot, therefore, transalkylate with benzene to produce ethylbenzene. Another advantage of this embodiment is that the polyethylbenzene column overhead stream does not contain the heaviest polyethylbenzenes that are produced in the alkylation-transalkylation reactors because the polyethylbenzene column is operated so as to reject the heaviest polyethylbenzenes in the polyethylbenzene column bottom stream. The absence of the heaviest polyethylbenzenes from the stream that is recycled to the alkylation-transalkylation reactors reduces the deactivation rate of the alkylation-transalkylation catalyst because the heavy polyethylbenzenes tend to foul the active sites of the catalyst.

In FIG. 1, a stream comprising ethylene enters the process in a line 14 and is admixed with a stream flowing through a line 15 that comprises benzene, diethylbenzenes, and triethylbenzenes, thereby producing a first alkylation-transalkylation reactor feed stream carried by a line 16. The benzene that is present in the stream flowing through the line 15 is benzene that has been added as make-up to the process and benzene that has been recycled within the process. Make-up benzene can enter the process in a line 10, admix with a stream flowing through a line 12, and flow into the line 15. Recycle benzene can flow from a benzene column 40, flow through a line 44, admix with a recycled polyethylbenzene column overhead stream flowing in a line 68, flow through the line 12, and flow into the line 15. The recycle polyalkylbenzenes flowing in the line 15 comprise diethylbenzenes and triethylbenzenes from the polyethylbenzene column overhead stream. Thus, the first alkylation-transalkylation reactor feed stream flowing through the line 16 contains ethylene, benzene, diethylbenzenes, and triethylbenzenes. The first reactor feed stream flowing through line 16 may be heated in a heat exchanger or a heater, which is not shown, and enters a first alkylation-transalkylation reactor 20. The first reactor feed stream contacts a zeolite beta catalyst maintained at reaction conditions to form ethylbenzene by alkylating benzene with at least a portion of the ethylene and by transalkylating benzene with at least a portion of the diethylbenzenes or triethylbenzenes. The first alkylation-transalkylation reactor effluent stream comprises benzene, ethylbenzene, by-products of the alkylation of benzene with ethylene, and by-products of the alkylation and transalkylation of diethylbenzenes and triethylbenzenes in the first reactor feed stream. Typically, the by-products in the first reactor effluent stream comprise diethylbenzenes, triethylbenzenes, butylbenzenes, dibutylbenzenes, tributylbenzenes, ethylbutylbenzenes, diethylbutylbenzenes, and diphenylethane. The first reactor effluent stream exits the first reactor 20 in a line 18.

The first alkylation-transalkylation reactor effluent stream enters a heat exchanger 22, where the first reactor effluent stream is cooled by exchanging heat indirectly with boiler feed water to produce low pressure steam. The cooled first reactor effluent stream passes through a line 24 and is admixed with ethylene that enters the process in a line 26. This produces a second alkylation-transalkylation reactor feed stream carried by a line 28. The second alkylation-transalkylation reactor feed stream may be heated in a heat exchanger or a heater, which is not shown, and enters a second alkylation-transalkylation reactor 30. The second reactor feed stream contacts a zeolite beta catalyst to alkylate benzene with ethylene and to transalkylate benzene with diethylbenzenes and triethylbenzenes in order to produce ethylbenzene. The second alkylation-transalkylation reactor effluent stream can include not only by-products of the alkylation of benzene with ethylene and of the transalkylation of benzene with diethylbenzenes and triethylbenzenes but also by-products of the alkylation and transalkylation of components of the first alkylation-transalkylation reactor effluent stream because the first alkylation-transalkylation reactor effluent stream is passed to the second alkylation-transalkylation reactor 30. Typically, the by-product in the second reactor effluent stream comprise those by by-products listed previously as being in the first reactor effluent stream. The second reactor effluent stream exits the second alkylation-transalkylation reactor 30 in a line 32. The second alkylation-transalkylation reactor effluent stream may be depressured by passing through a pressure control valve which is not shown, may be heated in a heater or heat exchanger which is also not shown, or both. The second alkylation-transalkylation reactor effluent then enters a benzene column 40.

The benzene column 40 separates the second alkylation-transalkylation reactor effluent stream by distillation into two streams. A benzene column overhead stream comprising benzene exits the benzene column through the line 44 and is recycled to the first alkylation-transalkylation reactor 20 as described previously. A benzene column bottom stream comprising the product ethylbenzene and the by-products including polyethylbenzenes exits the benzene column in a line 42 and enters an ethylbenzene column 50.

The ethylbenzene column 50 separates the benzene column bottom stream by distillation into two streams. An ethylbenzene column overhead stream comprising the product ethylbenzene exits the ethylbenzene column 50 in a line 52 and is recovered from the process. An ethylbenzene column bottom stream comprises by-product ethylbenzenes, typically including diethylbenzenes, triethylbenzenes, butylbenzenes, dibutylbenzenes, tributylbenzenes, ethylbutylbenzenes, diethylbutylbenzenes, and diphenylethane. The ethylbenzene column bottom stream exits the ethylbenzene column 50 in a line 54, and passes to a polyethylbenzene column 60.

The polyethylbenzene column 60 separates the ethylbenzene column bottom stream into two streams. A polyethylbenzene column bottom stream comprising polyethylbenzenes heavier than triethylbenzene exits from the bottom of the polyethylbenzene column 60 in a line 82 and is rejected from the process. The polyethylbenzene column overhead stream comprising diethylbenzenes and triethylbenzenes exits the polyethylbenzene column 60 in the line 68 and recycles to the first alkylation-transalkylation reactor 20 as described previously.

FIG. 2 illustrates another embodiment of this invention in which the second alkylation-transalkylation reactor effluent stream rather than the polyethylbenzene column overhead stream is recycled to the first alkylation-transalkylation reactor. One of the advantages of this embodiment in which a portion of the second alkylation-transalkylation reactor effluent stream. is recycled is because at least in theory the second alkylation-transalkylation reactor effluent stream can be recycled at a rate that is limited only by economic considerations. Except for the portion of the second alkylation-transalkylation reactor effluent stream that is passed downstream to product separation facilities, the second alkylation-transalkylation reactor effluent stream is available for recycle in what amounts to an unlimited quantity. Just as importantly, and unlike other streams in the process, the second alkylation-transalkylation reactor effluent stream can be recycled to the alkylation-transalkylation reactors without interfering with the extent to which the alkylation and transalkylation reactions proceed.

Referring now to FIG. 2, make-up ethylene enters the process in a line 114 and combines with a stream flowing through a line 115 that is formed from make-up benzene from a line 110, recycle benzene from a benzene column 140 via lines 144 and 112, and a recycled portion of the second alkylation-transalkylation reactor effluent stream via lines 136 and 112. Thus, the stream flowing through the line 115 carries at least one recycle polyalkylbenzene comprising at least two $C_2$ groups, such as diethylbenzenes, triethylbenzenes, and heavier polyalkylbenzenes. Whether any or all of these recycle polyalkylbenzenes is in fact present in the stream in line 115 depends on which of these recycle polyalkylbenzenes is present in the portion of the second alkylation-transalkylation reactor effluent stream that is recycled through the line 136. Accordingly, in this embodiment the first alkylation-transalkylation reactor feed stream flowing through the line 116 contains ethylene, benzene, and components of the second alkylation-transalkylation reactor effluent stream, including polyethylbenzenes. Polyethylbenzenes in the second alkylation-transalkylation reactor effluent stream can include not only by-products of the alkylation of benzene with ethylene but also by-products of the alkylation and transalkylation of various components of the second alkylation-transalkylation reactor effluent stream because the second alkylation-transalkylation reactor effluent stream is itself recycled to the first alkylation-transalkylation reactor 120. The first alkylation-transalkylation reactor feed stream flows through a line 116 and enters first alkylation-transalkylation reactor 120. The first alkylation-transalkylation reactor effluent stream exits the first alkylation-transalkylation reactor 120 in a line 118, is cooled in a heat exchanger 122, passes through a line 124, and combines with make-up ethylene from a line 126 to produce the second alkylation-transalkylation reactor feed stream. The second alkylation-transalkylation reactor feed stream enters a second alkylation-transalkylation reactor 130 through a line 128. The second alkylation-transalkylation reactor effluent stream exits the second alkylation-transalkylation reactor 130 in a line 132. A portion of the second alkylation-transalkylation reactor effluent stream is cooled in a heat exchanger or a cooler, which is not shown, and is recycled to the first alkylation-transalkylation reactor 120 through the lines 136, 112, 115, and 116. Another portion of the second alkylation-transalkylation reactor effluent stream passes through a line 134. This other portion of the second alkylation-transalkylation reactor effluent stream may be depressured, heated, or both, and then enters a benzene column 140.

The benzene column 140 separates the second reactor effluent stream into a benzene column overhead stream comprising benzene that is recycled to the first alkylation-transalkylation reactor 120 via the line 144 as described previously and into a benzene column bottom stream comprising ethylbenzene and by-product alkylbenzenes that flows through a line 142 to an ethylbenzene column 150. The ethylbenzene column 150 separates the benzene column bottom stream into an ethylbenzene column overhead stream comprising ethylbenzene that is recovered from the process through a line 152 and into an ethylbenzene column bottom stream comprising by-product alkylbenzenes such as diethylbenzenes, triethylbenzenes, butylbenzenes, dibutylbenzenes, tributylbenzenes, ethylbutylbenzenes, diethylbutylbenzenes, and diphenylethane. The ethylbenzene column bottom stream flows through a line 154 and is rejected from the process.

FIG. 3 illustrates another embodiment of this invention in which the ethylbenzene column bottom stream, rather than the second reactor effluent stream or the polyethylbenzene column overhead stream, is recycled to the first reactor. One of the advantages of this embodiment is that the bottom stream of the ethylbenzene column contains a relatively low concentration of ethylbenzene, which is not a polyalkylbenzene and cannot transalkylate with benzene to produce ethylbenzene. In addition, the absence of ethylbenzene from the stream that is recycled to the first alkylation-transalkylation reactor promotes the formation of ethylbenzene in the reactors because of the equilibrium between benzene, ethylene, and ethylbenzene. On the other hand, in comparison with the polyethylbenzene column overhead stream, the ethylbenzene column bottoms stream contains a relatively high concentration of polyalkylbenzenes, which tend to increase the deactivation rate of the alkylation-transalkylation catalyst.

Referring now to FIG. 3, make-up ethylene enters the process in a line 214 and combines with a stream flowing through a line 215 that is formed from make-up benzene from a line 210, a recycled portion of a benzene column overhead stream via lines 244 and 212, and a recycled portion of the ethylbenzene column bottom stream via lines 254, 258, and 212. Thus, the feed stream in line 216 to first alkylation-transalkylation reactor 220 contains ethylene, benzene, and components that are present in the ethylbenzene column bottom stream such as diethylbenzenes, triethylbenzenes, butylbenzenes, dibutylbenzenes, tributylbenzenes, ethylbutyl-benzenes, diethylbutylbenzenes, and diphenylethane. The first alkylation-transalkylation reactor effluent stream exits the first alkylation-transalkylation reactor 220 in a line 218, is cooled in a heat exchanger 222, passes through a line 224, and combines with make-up ethylene from a line 226 to produce the second alkylation-transalkylation reactor feed stream. The second alkylation-transalkylation reactor feed stream enters a second alkylation-transalkylation reactor 230 through a line 228. The second alkylation-transalkylation reactor effluent stream exits the second alkylation-transalkylation reactor 230 via a line 232 and enters a benzene column 240.

The benzene column 240 produces the benzene column overhead stream comprising benzene in the line 244 which is recycled to the first alkylation-transalkylation reactor 220 as described previously and a benzene column bottom stream comprising the product ethylbenzene and by-product alkylbenzenes that flows through a line 242 to an ethylbenzene column 250. An ethylbenzene column overhead stream comprising ethylbenzene is recovered from the process through a line 252. An ethylbenzene column bottom stream comprising by-product alkylbenzenes such as diethylbenzenes, triethylbenzenes, butylbenzenes, dibutylbenzenes, tributylbenzenes, ethylbutylbenzenes, diethylbutylbenzenes, and diphenylethane flows through a line 254. A portion of the ethylbenzene column bottom stream is recycled via the line 258 to the first alkylation-transalkylation reactor 220 as described previously. A small part of the ethylbenzene column bottoms stream is removed from the process via a line 256 in order to provide a purge for heavy polyalkylbenzenes.

Other embodiments of this invention include combinations of the three just-described embodiments. For example, instead of only one stream, two or three streams can be recycled to the first alkylation-transalkylation reactor. Thus, for example, in FIG. 1, a portion of the effluent stream of the second alkylation-transalkylation reactor 30 or a portion of the bottoms stream of the ethylbenzene column 50, or both, can be recycled to the first alkylation-transalkylation reactor 20.

EXAMPLES

Catalyst A is fresh alkylation catalyst comprising zeolite beta.

A sample of Catalyst A was used to produce ethylbenzene by alkylating benzene with ethylene at alkylation conditions at which heavy alkylaromatics were occluded on the surface and within the internal pore space of the sample of Catalyst A. After having been used for alkylation, the sample of Catalyst A had a content of occluded heavy alkylaromatics of about 5% by weight of the catalyst weight. While being contacted with air, the sample of Catalyst A having occluded heavy alkylaromatics was heated from ambient temperature to 1202° F. (650° C.) over a period of three hours, was maintained at 1202° F. (650° C.) for three hours, and then was cooled to room temperature. The sample of Catalyst A after cooling is referred to in these Examples as Catalyst B.

Catalyst C is a fresh alkylation catalyst comprising zeolite beta.

Catalyst D is a fresh alkylation catalyst comprising 80 wt-% 'ultrastabilized' zeolite Y and 20 wt-% alumina binder.

In the Examples 1-9 that follow, the net reactor effluent stream is the total reactor effluent stream less the portion, if any, of the total reactor effluent stream that is recycled to the reactor. Efficiency is defined with respect to ethylene and is computed by subtracting the weight of ethylene in the net reactor effluent stream from the weight of ethylene in the make-up ethylene to the reactor, divided by the weight of ethylene in the net reactor effluent stream, times 100. Selectivity of 1,1-DPE is defined as the concentration in weight percent of 1,1-DPE in the net reactor effluent stream, computed on the basis of the net reactor effluent stream being free of benzene and light compounds. In general, the yield of a compound is defined as the product of conversion and selectivity of that compound, divided by 100. However, the ethylbenzene yield has a special definition in that it is defined as the sum of the individual yields of ethylbenzene, diethylbenzene, and triethylbenzene. This computation of the ethylbenzene yield accounts for the total yield of ethylbenzene that would be produced if all the diethylbenzene and triethylbenzene in the product stream was transalkylated to ethylbenzene in a transalkylation zone and subsequently recovered.

In addition, in the Examples 1-9 the benzene liquid hourly space velocity (LHSV) is computed using only the make-up benzene and does not include the benzene in the portion, if any, of the total reactor effluent stream that is recycled to the catalyst bed. Also, because the molar ratio of phenyl groups per ethyl group (or per propyl group) is essentially the same in the total reactor feed stream and the total reactor effluent stream, the molar ratio of phenyl groups per ethyl group (or per propyl group) is not significantly affected by recycling any portion of the total reactor effluent stream.

In Examples 1-7, the catalyst is contacted with a combined feed stream containing fresh benzene, fresh ethylene, a recycled aliquot portion of the reactor effluent stream (in Examples 1, 3, 5, 6, and 7 only), and fresh diethylbenzene (in Example 6 only). Where a portion of the reactor effluent stream is recycled to the reactor, the ratio of the weight of the recycled portion of the reactor effluent stream per the weight of fresh benzene and fresh ethylene was 2.0.

TABLE 1

Effect of Ethylene Concentration on 1,1-DPE Formation at Various Molar Ratios of Phenyl Groups per Ethyl Group using Zeolite Beta Catalysts

| Example | 1 | 2 | 3 | 4 | 5 | 6 | 7 |
|---|---|---|---|---|---|---|---|
| Catalyst | B | B | B | B | B | A | A |
| Phenyl/Ethyl, mol/mol | 5.21 | 5.25 | 4.09 | 4.27 | 1.81 | 4.54 | 4.55 |
| Maximum temp., ° C. | 241.9 | 252.5 | 201.7 | 252.1 | 231.8 | 242 | 242 |
| Temp. rise, ° C. | 15.9 | 33.3 | 20.9 | 34.7 | 24.1 | 23.4 | 25.5 |
| Pressure, psi(g) | 550 | 550 | 550 | 550 | 550 | 550 | 550 |
| Benzene LHSV, hr$^{-1}$ | 3.9 | 4.1 | 2.6 | 3.3 | 1.3 | 3.9 | 2.9 |
| Recycle effluent/fresh feed, wt/wt | 2.0 | 0 | 2.0 | 0 | 2.0 | 2.0 | 2.0 |
| Ethylene concentration in combined feed wt-% | 2.15 | 6.4 | 2.79 | 7.75 | 5.52 | 1.88 | 2.44 |
| EB yield, wt-% | 99.82 | 99.79 | 99.83 | 99.73 | 98.24 | 99.49 | 99.38 |
| 1,1-DPE selectivity, wppm | 886 | 928 | 895 | 1230 | 11180 | 2900 | 3100 |
| 1,1-DPE/EB in reactor effluent (wt-%/wt-%) × 10$^2$ | .101 | .105 | .105 | .143 | 1.74 | .357 | .348 |
| Ethylene efficiency, wt-% | 99.9 | 99.9 | 99.9 | 99.9 | 99.5 | 99.8 | 99.8 |

A comparison of Examples 1 and 2 shows the effect of recycling a portion of the reactor effluent stream to the reactor in order to decrease the concentration of ethylene in the feed stream at nearly the same molar ratio of phenyl groups per ethyl group (5.21 and 5.25). Recycling a portion of the effluent stream in Example 1 increases the ethylbenzene yield, decreases the 1,1-DPE selectivity, and decreases the ratio of 1,1-DPE per ethylbenzene in the effluent stream.

A comparison of Examples 3 and 4 shows the effect of recycling a portion of the reactor effluent stream to the reactor in order to decrease the concentration of ethylene in the feed stream at molar ratios of phenyl groups per ethyl group (4.09 and 4.27) that are lower than in Examples 1 and 2. Recycling a portion of the reactor effluent stream in Example 3 increases the ethylbenzene yield, decreases the 1,1-DPE selectivity, and decreases the ratio of 1,1-DPE per ethylbenzene in the effluent stream, even though the molar ratio of phenyl groups per ethyl group is lower in Example 3 than in Example 4.

Example 5 shows the effect of recycling a portion of the reactor effluent stream to the reactor at a lower molar ratio of phenyl groups per ethyl group than in Examples 1 through 4, but without decreasing the concentration of ethylene in the feed stream. With the concentration of ethylene in the feed stream being relatively high at 5.52 wt-%, then even though the molar ratio of phenyl groups per ethyl group is 1.81:1, the ethylbenzene yield is lower, the 1,1-DPE selectivity is higher, and the ratio of 1,1-DPE per ethylbenzene in the effluent stream is higher than in Examples 1 through 4.

In Example 6, fresh diethylbenzene was passed to the reactor in order to simulate the effect of recycling diethylbenzene. Fresh diethylbenzene constituted 4.5 wt-% of the weight of the fresh benzene, fresh ethylene, and fresh diethylbenzene that was passed to the reactor. The molar ratio of phenyl groups per ethyl group of 4.54 takes into account the phenyl and ethyl groups of the fresh diethylbenzene. A comparison of Examples 6 and 7 shows the effect of introducing diethylbenzene to the reactor while recycling a portion of the effluent stream to the reactor at nearly the same molar ratios of phenyl groups per ethyl group. Introducing diethylbenzene increases the ethylbenzene yield and decreases the 1,1 -DPE selectivity.

In Examples 8 and 9, the catalyst is contacted with a combined feed stream containing fresh benzene, fresh propylene, and a recycled aliquot portion of the reactor effluent stream. The ratio of the weight of the recycled portion of the reactor effluent stream per the weight of fresh benzene and fresh propylene was 1.5 in Example 8 and 1.75 in Example 9. The position of the maximum temperature (due to the exothermic reaction) in the catalyst bed was noted. Deactivation was determined by noting the position of the maximum temperature after a suitable interval of time (e.g., 48 hours) at test conditions. Deactivation is calculated by taking the difference in these two positions (in inches), dividing by the bed length (in inches), and then dividing by the time interval (in days). The results are multiplied by 100% to give a deactivation rate in percent of catalyst bed/day.

TABLE 2

Effect of Recycling Reactor Effluent on Catalyst Deactivation Rate at the Same Phenyl/Propyl Ratio using Zeolite Beta Catalyst

| Example | 8 | 9 |
|---|---|---|
| Catalyst | C | C |
| Phenyl/Propyl, mol/mol | 4 | 4 |
| Maximum temp., ° C. | 180 | 180 |
| Temp. rise ° C. | 25 | 23 |
| Pressure, psi(g) | 500 | 500 |
| Benzene LHSV, hr$^{-1}$ | 4 | 4 |
| Recycle effluent/fresh feed, wt/wt | 1.5 | 1.75 |
| Propylene concentration in combined feed, wt-% | 4.7 | 4.3 |
| Deactivation rate, %/day | 3.45 | 2.86 |

A comparison of Examples 8 and 9 shows that increasing the recycle ratio of the effluent stream to the catalyst bed at the same molar ratio of phenyl groups per propyl group decreases the rate of catalyst deactivation. Although these data showing a decrease in the deactivation rate were obtained while Catalyst C was used to alkylate benzene with propylene, it is believed that a similar decrease in the rate of catalyst deactivation would be observed if Catalyst C is used to alkylate benzene with ethylene.

In Examples 10 and 11, the catalyst is contacted with a combined stream comprising fresh benzene, fresh ethylene, and a recycled aliquot portion of the reactor effluent stream (in Example 10 only). In Example 10, the ratio of the weight of the recycled portion of the reactor effluent stream per the weight of fresh benzene was 3. Deactivation rates were determined by the calculation method described previously for Examples 8 and 9.

TABLE 3

Effect of Recycling Reactor Effluent on 1,1-DPE Formation and on Catalyst Deactivation Rate at the Same Phenyl/Ethyl Ratio Using Zeolite Y Catalyst

| Example | 10 | 11 |
|---|---|---|
| Catalyst | D | D |
| Phenyl/Ethyl, mol/mol | 5.0 | 5.0 |
| Maximum temp., ° C. | 240 | 240 |
| Pressure, psi(g) | 550 | 550 |
| Ethylene LHSV, hr$^{-1}$ | 0.3 | 0.3 |
| Recycle effluent/fresh benzene, wt/wt | 3 | 0 |
| 1,1-DPE/EB in reactor effluent, (wt-%/wt-%) × 10$^2$ | 2.76 | 2.45 |
| Deactivation rate, %/day | 2.5 | 1.7 |

A comparison of Examples 10 and 11 shows that increasing the recycle ratio of the effluent stream to the catalyst bed at the same molar ratio of phenyl groups per ethyl group increases the ratio of 1,1-DPE per ethylbenzene in the effluent stream and increases the rate of catalyst deactivation. Thus, in contrast to zeolite beta, zeolite Y's performance worsens as a result of recycling reactor effluent.

Examples 12 and 13 are illustrative of a preferred catalyst for use in this invention.

Example 12

Preparation of acid washed zeolite betas. To a solution of 1428 grams ammonium nitrate in 3224 grams distilled water was added 932 grams of 70 weight percent nitric acid and the mixture was heated to 85° C. A dry weight of 1416 grams of commercial zeolite beta, SiO$_2$ 92.2 wt-%, Al$_2$O$_3$ 7.0 wt-%, LOI 24.3 wt-%, and N$_2$ BET 672 m$^2$/g, was added and this mixture was stirred at 85° C. for 90 minutes. The slurry was filtered and washed using 10 liters of distilled water and then dried at 100° C. for 16 hours. After drying, the material was calcined at 650° C. for 3 hours in air. Analyses of this sample showed 91.7 wt-% SiO$_2$, 6.1 wt-% Al$_2$O$_3$, and a molar ratio SiO$_2$/Al$_2$/O$_3$ of 25.5. The sample was examined by x-ray photoelectron spectroscopy (XPS) to determine binding energies, as well as the surface silicon: aluminum atomic ratio. The results are summarized in Table 4.

TABLE 4

| Peak | Binding Energies (eV) |
|---|---|
| Al2p | 75.20 |
| Si2p | 103.30 |
| O 1s | 532.43 |

TABLE 4-continued

| | Peak Surface Concentrations (atomic %) |
|---|---|
| Al | 1.93 |
| Si | 29.91 |
| Si/Al (bulk) | ≈13 |
| Si/Al (XPS) | 16 |

Example 13

Alkylation of benzene with propylene. The sample described in Example 12 was bound with alumina (70/30 zeolite/binder), extruded (1/16" extrudates), dried, and then calcined at 650° C. for 2 hours. 10 cc of 1/16" extrudates were loaded into a reactor to form a bed ½" in diameter and 3 ¾" to 4" long. The catalyst was activated for 12 hours by passing a stream of benzene over the catalyst at 140° C., 500 psig, and 6 benzene LHSV. Temperature was adjusted to the desired run temperature and the feed switched to a blend of 6 weight percent propylene in benzene at 6 LHSV. The position of the maximum temperature (due to the exothermic reaction) in the bed was noted. The deactivation rate was determined by the calculation method described previously for Examples 8 and 9. The catalyst was tested at 130° C., and the deactivation rate was 10.3% per day.

Example 14

A feed stream was prepared containing benzene and ethylene and having a molar ratio of benzene per ethylene of about 6:1. For this feed stream, the molar ratio of phenyl groups per ethyl groups is equal to the molar ratio of benzene per ethylene. The feed stream was contacted with zeolite beta in a reactor at a temperature of 252° C. (486° F.), at a weight hourly space velocity of 7.5 hr$^{-1}$, and at a pressure of 565 psia that was sufficient to maintain the benzene and the ethylene in the liquid phase. A first portion of the effluent stream from the reactor was cooled, recycled, and combined with the feed stream at a weight ratio of effluent recycle to feed stream of 2:1. A second portion of the effluent stream, which was recovered as product from the reactor, contained about 18 wt-% ethylbenzene and about 1.5 wt-% diethylbenzene.

Example 15

An aromatic stream was prepared containing 95.5 wt-% benzene and 4.5 wt-% para-diethylbenzene. A feed stream was prepared by admixing the aromatic stream with ethylene to attain a molar ratio of phenyl groups per ethyl groups of about 4.5:1. For this feed stream, the molar ratio of phenyl groups per ethyl groups is less than the molar ratio of benzene per ethylene, because of the presence of paradiethylbenzene. The feed stream was contacted with zeolite beta in a reactor at a temperature of 252° C. (486° F.), at a weight hourly space velocity of 7.5 hr$^{-1}$, and at a pressure of 565 psia that was sufficient to maintain the benzene and the ethylene in the liquid phase. A first portion of the effluent stream from the reactor was cooled, recycled, and combined with the feed stream at a weight ratio of effluent recycle to feed stream of 2:1. A second portion of the effluent stream, which was recovered as product from the reactor, contained about 21 wt-% ethylbenzene and about 3.5 wt-% diethylbenzene. The molar ratio of meta-diethylbenzene per para-diethylbenzene in the product was about 2.2:1.

A comparison of Examples 14 and 15 shows that in Example 15 a significant quantity of diethylbenzene converted to ethylbenzene by transalkylation. If no diethylbenzene had transalkylated, the product in Example 15 would have contained about 6.0 wt-% diethylbenzene, which is the sum of the 1.5 wt-% diethylbenzene in the product of Example 14 plus the 4.5 wt-% diethylbenzene in the feed stream of Example 15. In fact, the product in Example 15 contained about 3.5 wt-% diethylbenzene. The difference between 6.0 wt-% and 3.5 wt-% is attributable to transalkylation of diethylbenzene in Example 15.

In addition, Example 15 also shows that the para-diethylbenzene in the feed isomerized to meta-diethylbenzene almost to the extent that would be predicted by equilibrium at the conditions of Example 15. Therefore, these results indicate that the conclusion that transalkylation occurred at the conditions of Example 15 applies not only to the case where the feed stream contains para-diethylbenzene, but would also apply to the case where the feed stream contains meta-diethylbenzene or ortho-diethylbenzene. This is because even if the feed stream had contained meta-diethylbenzene or ortho-diethylbenzene instead of para-diethylbenzene, these other isomers would have isomerized to para-diethylbenzene and the experimental results would have been the same.

Example 16

Example 15 was repeated, except that the reaction temperature was 242° C. (468° F.) instead of 252° C. (486° F.). The product contained about 4.2 wt-% diethylbenzene instead of about 3.5 wt-% diethylbenzene.

A comparison of Examples 15 and 16 shows that a decrease in temperature decreases the quantity of diethylbenzene converted to ethylbenzene by transalkylation. Because increasing the weight ratio of effluent recycle to feed stream with all other variables constant tends to decrease the reaction temperature, Example 16 indicates that an increase in weight ratio of effluent recycle to feed stream would decrease the quantity of diethylbenzene converted to ethylbenzene by transalkylation. Likewise, a decrease in weight ratio of effluent recycle to feed stream would increase the quantity of diethylbenzene converted to ethylbenzene by transalkylation. Of course, the change in reaction temperature that occurs as a result of the change in weight ratio of effluent recycle to feed stream could be compensated for by a change in the amount of heat added or removed from the reactor.

What is claimed is:

1. A prooess for producing an monoalkyl aromatic comprising:
   a) passing a feed aromatic, an olefin, and a polyalkyl aromatic comprising at least one phenyl group and at least two alkyl groups corresponding to said olefin to a reaction zone;
   b) alkylating said feed aromatic with said olefin and transalkylating said feed aromatic with said polyalkyl aromatic in said reaction zone in the presence of zeolite beta to form a monoalkyl aromatice;
   c) Inhibiting the formation of diarylalkane corrsponding to said olefin by operating said reaction zone at reaction conditions comprising a temperature of from about 100° C. to about 475° C. a pressure sufficient to maintain said feed aromatice in at least a partial liquid phase, a molar ratio of phenyl groups per alkyl group corresponding to said olefin olefin of from bout 0.75:1 to about 25:1, and a concentration of said olefin, based on the weight of said feed aromatic said olefin, and said polalkyl aromatic passed to said reaction zone in Step (a), of less than $$\frac{MW_O}{6.17 \times MW_A + MW_O}, \text{wt}-\%$$

wherein $MW_O$ is the molecular weight of said olefin and $MW_A$ is the molecular weight of said feed aromatic and d) withdrawing from said reaction zone a product comprising said monoalkyl aromatic.

2. The process of claim 1 wherein said polyalkyl aromatic is selected from the group consisting of alkylated derivatives of benzene, alkylated derivatives of naphthalene, alkylated derivatives of anthracene, and alkylated derivatives of tetralin.

3. The process of claim 1 wherein said feed aromatic is selected from the group consisting of benzene, naphthalene, anthracene, tetralin, and alkylated derivatives thereof.

4. The process of claim 1 wherein said olefin has from 2 to about 20 carbon atoms.

5. The process of claim 1 wherein said olefin is propylene, said feed aromatic is benzene, said monoalkyl aromatic is cumene, and said diarylalkane is 2,2-diphenylpropane.

6. The process of claim 1 wherein said molar ratio is less than 6:1.

7. The process of claim 1 wherein said product contains less than 1.0 wt-% diarylalkane relative to said monoalkyl aromatic.

8. The process of claim 1 wherein said product comprises said polyalkyl aromatic, and said polyalkyl aromatic is separated from said product and recycled to provide at least a portion of said polyalkyl aromatic in Step (a).

9. The process of claim 1 wherein said polyalkyl aromatic comprises a diethylbenzene and said reaction conditions are sufficient to isomerized diethylbenzene.

10. The process of claim 1 wherein said zeolite beta comprises a calcined, non-templated surface-modified zeolite beta characterized by having surface aluminum 2p binding energies, as measured by X-ray photoelectron spectroscopy, of at least 74.8 electron volts.

11. A process for producing ethylbenzene comprising:
a) passing benzene, ethylene, and a polyalkyl aromatic comprising at least one phenyl group and at least two ethyl groups to a reaction zone;
b) alkylating benzene with ethylene and transalkylating benzene with said polyalkyl aromatic in said reaction zone in the presence of zeolite beta to form ethylbenzene at reaction conditions comprising a molar ratio of phenyl groups per ethyl group of from about 1:1 to about 6:1 and a concentration of ethylene of less than 5.5 wt-%;
c) withdrawing from said reaction zone a product comprising ethylbenzene and said polyalkyl aromatic and containing less than 1.0 wt-% 1,1-diphenylethane relative to ethylbenzene;
(d) separating said polyalkyl aromatic from said product; and
(e) recycling said polyalkyl aromatic to Step (a).

12. The process of claim 11 further characterized in that said polyalkyl aromatic is selected from the group consisting of a diethylbenzene, a triethylbenzene, a tetraethylbenzene, or a diethylbutylbenzene.

13. A process for the production of ethylbenzene, said process comprising the steps of:
(a) combining ethylene, an input stream comprising benzene, and a recycle stream comprising diethylbenzene to form a combined stream, passing said combined stream to a reaction zone containing a catalyst comprising zeolite beta at reaction conditions sufficient to alkylate benzene with ethylene sand to transalkylate benzene with diethylbenzene and comprising a molar ration of phenyl groups per ethyl group of from about 1:1 to about 6:1 and a concenetration of ethylene of less than 5.5 wt-%, and recovering from said reaction zone an effluent stream comprising benzene, ethylbenzene, diethlbenzene, and a heavy polyalkylaromatic and containing less than 1.0 wt-% 1,1-diphenylethance relative to ethylbenzene;
(b) passing at least a portion of said effluent stream to a separation zone, separating said effluent stream and withdrawing from said separation zone a low-boiling fraction comprising benzene a product stream comprising ethylbenzene that is recovered from said process, and a high-boiling fraction comprising diethylbenzene and said heavy polyalkylaromatic;
(c) providing a portion of said input stream from at least a portion of said low-boiling fraction; and
(d) forming said recycle stream from at least one of a portion of said effluent stream and at least a portion of said high-boiling fraction.

14. The process of claim 13 further characterized in that said high-boiling fraction is passed to a distillation zone and is separated into an overhead stream comprising diethylbenzene and a bottom stream comprising said heavy polyalkylaromatic, and at least a portion of said overhead stream forms said recycle stream.

15. The process of claim 14 further characterized in that said overhead stream comprises triethylbenzene.

16. The process of claim 13 further characterized in that said portion of said effluent stream in Step (d) is cooled to produce a cooled effluent stream, and said cooled effluent stream provides at least a portion of said recycle stream.

* * * * *

UNITED STATES PATENT AND TRADEMARK OFFICE
CERTIFICATE OF CORRECTION

PATENT NO. : 6,043,402　　　　　　　　　　　　　　　　　　Page 1 of 1
DATED : March 28, 2000
INVENTOR(S) : Gregory J. Gajda It is certified that error appears in the above-identified patent and that said Letters Patent is hereby corrected as shown below:

Column 22,
Line 60, "Inhibiting" should be replaced with -- inhibiting.--
Line 66, "bout" should be replaced with -- about --.

Column 23,
Line 36, "isomerized" should be replaced with "isomerize."

Column 24,
Line 19, "sand" should be replaced with "and".
Line 25, "diethlbenzene" should be replaced with -- diethylbenzene --.
Line 26, "diphenylethance" should be replaced with -- diphenylethane. --
Line 31, there should be a comma inserted after the word -- benzene --

Signed and Sealed this

Twelfth Day of February, 2002

Attest:

JAMES E. ROGAN
Attesting Officer　　　Director of the United States Patent and Trademark Office